United States Patent [19]

Kunz

[11] Patent Number: 4,963,583
[45] Date of Patent: Oct. 16, 1990

[54] BETA-IONONE DERIVATIVES AS ANTIFUNGAL AGENTS

[75] Inventor: Walter Kunz, Oberwil, Switzerland

[73] Assignee: Ciba-Geigy Corporation, Ardsley, N.Y.

[21] Appl. No.: 250,201

[22] Filed: Sep. 28, 1988

[30] Foreign Application Priority Data

Oct. 5, 1987 [GB] United Kingdom ............... 87 23325
May 26, 1988 [GB] United Kingdom ............... 88 12525

[51] Int. Cl.⁵ ................. C07C 125/065; C07C 69/03; A01N 37/02; A01N 47/18
[52] U.S. Cl. .................................. 514/484; 514/490; 514/531; 514/546; 560/115; 560/124; 560/160; 560/162; 560/187; 560/259; 558/234
[58] Field of Search ............... 560/124, 115, 161, 162, 560/187, 259, 160; 558/234, 276; 514/484, 490, 512, 531, 550, 546

[56] References Cited

FOREIGN PATENT DOCUMENTS 5749 12/1979 European Pat. Off. .
56-57734 5/1981 Japan .

OTHER PUBLICATIONS

Widmer et al. Helv. Chim. Acta, 64,2405-2418, (1981).
R. A. Leppek et al., Phylochemistry, 11, 2055-2063 (1972).
Annales du Tabac, 1974, 208.
Becher, Helv. Chim. Acta, 64(7), p. 2419-35, (1981).

*Primary Examiner*—Michael L. Shippen
*Attorney, Agent, or Firm*—Edward McC. Roberts; George R. Dohmann

[57] ABSTRACT

Novel 3-acyloxy-4-keto-β-ionone derivatives of the formula I

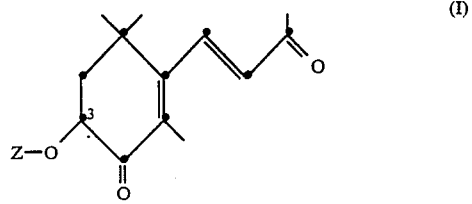
(I)

wherein Z is either the radical

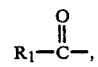

in which $R_1$ represents $C_2$-$C_5$ alkyl, $C_1$-$C_5$ alkoxy-$C_1$-$C_5$ alkyl having a maximum number of 6 carbon atoms, cyclopropyl or cyclopropyl which is substituted by methyl or by halogen or represents the radical

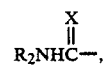

wherein $R_2$ represents $C_1$-$C_5$ alkyl, $C_1$-$C_5$ alkoxy-$C_1$-$C_5$ alkyl having a maximum number of 6 carbon atoms, cyclopropyl or cyclopropyl which is substituted by methyl or by halogen and X represents either oxygen or sulphur, and

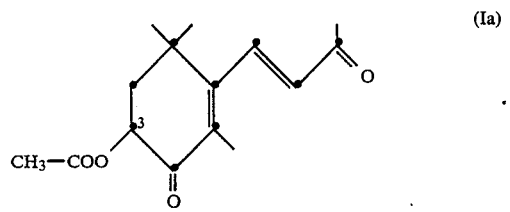
(Ia)

display very effective microbicidal activity. They can especially be used in microbicidal compositions to control plant-pathogenic microorganisms, preferably fungi of the order Oomycetes.

16 Claims, No Drawings

BETA-IONONE DERIVATIVES AS ANTIFUNGAL AGENTS

The present invention relates to novel derivatives of 3-hydroxy-4-keto-β-ionone of formula I and to the use of derivatives of 3-hydroxy-4-keto-β-ionone to control fungal infections. Furthermore, the invention also relates to the preparation of the novel compounds of the formula I and to compositions which contain at least one of these compounds as active ingredient.

In the formula I

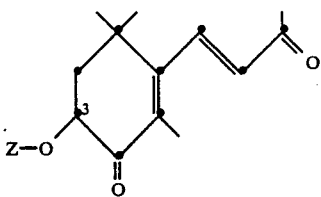
(I)

wherein Z is either the radical

in which $R_1$ represents $C_2$–$C_5$alkyl, $C_1$–$C_5$ alkoxy-$C_1$–$C_5$ alkyl having a maximum number of 6 carbon atoms, cyclopropyl or cyclopropyl which is substituted by methyl or by halogen or represents the radical

wherein $R_2$ represents $C_1$–$C_5$alkyl, $C_1$–$C_5$ alkoxy-$C_1$–$C_5$ alkyl having a maximum number of 6 carbon atoms, cyclopropyl or cyclopropyl which is substituted by methyl or by halogen and X represents either oxygen or sulphur.

Depending on the number of carbon atoms alkyl comprises n-butyl, isobutyl, sec.butyl, tert.butyl, n-pentyl, sec.pentyl, 1.1-dimethylpropyl, 2-methylbutyl, 2.2-dimethylpropyl, isopentyl (=3-methylbutyl) and 1-ethylpropyl. Accordingly, $C_1$–$C_5$ alkoxy comprises methoxy, ethoxy, n-propoxy, isopropoxy, n-butoxy, isobutoxy, sec.butoxy and tert.butoxy, n-pentoxy.

Preferred compounds are those wherein Z is the radical

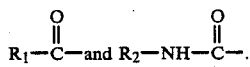

Specific mention should be made of compounds wherein $R_1$ is unbranched propyl, butyl and pentyl with n-propyl being preferred.

The compounds of formula I and the already known 3-acetoxy-4-keto-β-ionon of the formula Ia [Helv.-Chim.Acta 44, 2419 (1981)]

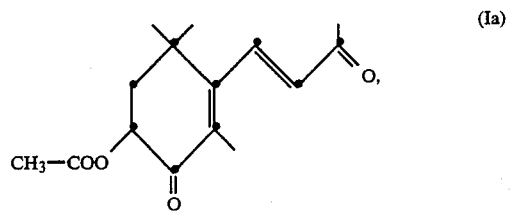
(Ia)

as well, are mainly oils which are stable at room temperature and have very valuable microbicidal properties. They can be used in agriculture or related fields preventively and curatively for controlling phytopathogenic microorganisms. The compounds of formula I are very well tolerated by cultivated plants.

In Phytochemistry 1972, Vol. 11, pp. 2055–2063 it has been reported that tobacco plants are capable of producing 3-iso-butyroxy-β-ionone, an inhibitor of the germination of *P. tabacina* conidia. The natural product 3-isobutyroxy-β-ionone has been named "Quiesone".

4-keto-β-ionones are described as tobacco flavour and/or aroma additives (U.S. Pat. No. 3,746,010 and Japanese Patent J5 6039-063).

In Annales du tabac, 1974, 208, it has been reported, that β-ionone is an inhibitor of the main phases of the *Peronosoora tabacina* cycle. However, the level of activity of β-ionone has not been proved to be sufficient for practical purposes. Surprisingly, it has now been found that the 3-alkanoyl-4-keto-β-ionone derivatives of the formula I and Ia display higher activities against Peronosporales and other plantpathogenic microorganisms than β-ionone does.

The activities of compounds of formula I and Ia are directed preferably to plant diseases caused by Oomycetes and among them especially to Peronosporales. One of the targets is *Peronospora tabacina*, a pathogen of tobacco causing blue mold. Blue mold is a major disease of tobacco worldwide. Another of the targets is the class of the Ascomycetes (e.g. Venturia, Podosphaera, Erysiphe, Monilinia, Uncinula). In addition, the compounds of formula I have a systemic action. They can also be used as dressing agents for protecting seeds (fruit, tubers, grains) and plant cuttings against fungus infections as well as against phytopathogenic fungi which occur in the soil.

The carboxyl group of the 4-keto-β-ionone derivatives of the formula I and Ia is linked to an asymmetric carbon atom in the ring. Provided that there is no additional asymmetric centre in the acyl moiety, the compounds will be obtained in the form of two enantiomers. Depending on the synthesis method, a mixture of both enantiomers or one single enantiomer can be prepared. Racemic 3(±)-hydroxy-4-keto-β-ionone can be resolved by standard methods, e.g. by acylation with an optical active acid derivative. After separation and cleavage of the resulting diastereomeric mixture, pure (R)- or (S)-3-hydroxy-4-keto-β-ionone can be obtained as described in Helvetica Chim. Acta 64, 2405 (1981).

Examples of useful optical active acid derivatives as chiral auxiliaries are e.g. camphanic acid (Helv. 51. 1587, (1968); camphorsulfonic acid (Tetrahedron Lett. 1969, 313); 3-β-acetoxy-Δ⁵-etienic acid (Tetrahedron 5, 70 (1959); J. Org. Chem. 33, 4242) or α-methoxy-α-trifluoromethylphenyl acetic acid (J. Am. Chem. Soc. 1973. 95, 239).

The enantiomers have different biological properties.

The present invention relates to all pure isomers of formula I as well as mixtures thereof.

Another aspect of the invention are microbicidal compositions containing, as at least one active ingredient, a compound of the formulas I or Ia, as well as the use of such compositions for controlling phytopathogenic microorganisms, especially harmful fungi, and for the preventive treatment of plants to protect them from attack by such microorganisms.

Still another aspect of the invention is a method of treating plants or parts of plants or the locus, which comprises applying thereto the compounds of formula I and Ia or the novel compositions.

Target crops to be protected within the scope of the present invention comprise e.g. the following species of plants: cereals (wheat, barley, rye, oats, rice, sorghum and related crops), beet (sugar beet and fodder beet), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites), areas of grass, embankments or general low cover crops which counteract erosion or desiccation of the soil and are useful in cultures of trees and perennials (fruit plantations, hop, plantations, maize fields, vineyards etc.).

The compounds of formula I are normally applied in the form of compositions and can be applied to the crop area or plant or substrate to be treated, simultaneously or in succession, with further compounds. These compounds can be both fertilisers or micronutrient donors or other preparations that influence plant growth. They can also be selective herbicides, fungicides, bactericides, nematicides, mollusicides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers. Phospholipids are also useful formulation assistants.

A preferred method of applying a compound of the formula I, or an agrochemical composition which contains at least one of said compounds, is foliar application. The number of applications and the rate of application depend on the risk of infestation by the corresponding pathogen (type of fungus). However, the compounds of formula I can also penetrate the plant through the roots via the soil (systemic action) by impregnating the locus of the plant with a liquid composition, or by applying the compounds in solid form to the soil, e.g. in granular form (soil application). The compounds of formula I may also be applied to seeds (coating) by impregnating the seeds either with a liquid formulation containing a compound of the formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 1000 g a.i./ha.

The formulations, i.e. the compositions or preparations containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

The compositions may also contain further ingredients such as stabilisers, antifoams, viscosity regulators, binders, tackifiers as well as fertilisers or other active ingredients in order to obtain special effects.

The surfactant customarily employed in the art of formulation are described e.g. in "McCutcheon's Detergents and Emulsifiers Annual", MC Publishing Corp. Ringwood, New Jersey, 1981.

The agrochemical compositions usually contain 0.1 to 99%, preferably 0.1 to 95%, of a compound of formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compounds of formula I, wherein Z is the radical

are obtained by conventional esterification of either racemic or enantiomeric pure 3(R)- or 3(S)-hydroxy-4-keto-β-ionone (formula II, IIa, IIb)

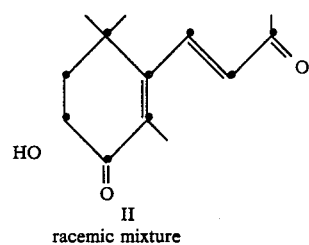

II
racemic mixture

-continued

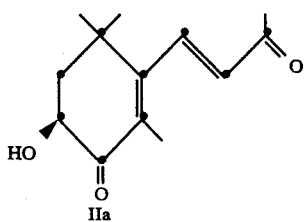
IIa
3(R)-isomer

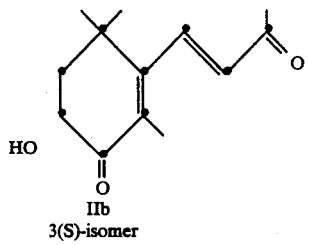
IIb
3(S)-isomer

The compounds of formula I, wherein Z is the radical

R₂NHC—, in which R₂ represents $C_1$–$C_5$-alkyl, $C_1$–$C_5$-alkoxy-$C_1$–$C_5$-alkyl with a maximum number of 6 carbon atoms, cyclopropyl or cyclopropyl which is substituted by methyl or by halogen, are obtained by reacting an isocyanate or thioisocyanate with a compound of the formulae II, IIa or IIb.

The starting material of formulae II, IIa and IIb are generally known compounds and can be prepared by known procedures.

The synthesis of the racemic compound II and of the pure 3(R) and 3(S) enantiomers of the formula IIa and IIb and of their acetates of the formula Ia are described in Helv.Chim.Acta 64, 2419 (1981).

Esterification (II→I) can be accomplished by treating 3-hydroxy-4-keto-β-ionone II, IIa or IIb with a carboxylic acid R₁COOH in the presence of an inorganic acid or with activators such as dicyclohexylcarbodiimide or diethyl azodicarboxylate/triphenylphosphine (Synthesis 1979, 561, ibid. 1981, 1).

Esterification can also be effected by treating either the alcohol II, IIa or IIb with a carboxylic acid halide or an anhydride, in a solvent such as tetrahydrofurane, dioxane, acetonitrile or dichloromethane, in the presence of a base, such as common tert. amine (e.g. triethylamine or pyridine) and, if necessary, with a catalytical amount of 4-dimethylaminopyridine.

The reaction with an isocyanate or a thioisocyanate of the formula R₂NCX can be accomplished in the presence of a catalytic amount of 1,4-diazabicyclo-2,2,2]-octane.

Both reactions are preferably carried out in inert solvents such as hydrocarbons, ether or nitriles (e.g. acetonitril). Pyridine can also be used as solvent. The temperature may be in the range of from −10° to +80° C., preferably at room or slightly elevated temperature.

1. Preparation examples
Preparation of the compound

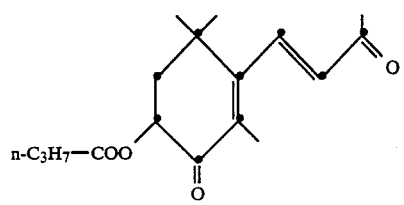

rac. 3-n-butyroyloxy-4-keto-β-ionone (Compound No. 2 of Table 1)

2.84 g (18 mmoles) butyric acid anhydride are added to a solution of 2.5 g (11.2 mmoles) rac. 3-hydroxy-4-keto-β-ionone [synthesized according to Helv. Chim. Acta 62, 2405 (1981)]. After stirring at room temperature, the reaction mixture is poured into a mixture of ice and water. The resulting mixture is extracted with ether, the extracts are combined and washed several times with aqueous sodium hydrogen carbonate and water. After drying over sodium sulfate, the solvent is stripped off. The remaining oil corresponds to the title compound. $n_D^{20}$:1.5152.

The compounds listed in the following table 1 can be prepared according to the method described above.

TABLE 1

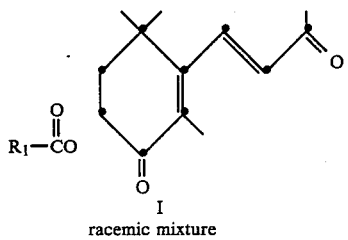
I
racemic mixture

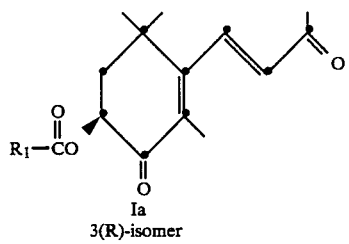
Ia
3(R)-isomer

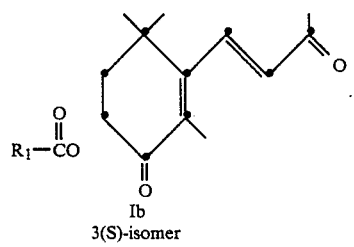
Ib
3(S)-isomer

| No. | R₁ | Configuration at C-3 | physical data |
|---|---|---|---|
| 1.1 | C₂H₅ | racemic mixture | |
| 1.1a | | R | |
| 1.1b | | S | |
| 1.2 | n-C₃H₇— | racemic mixture | $n_D^{20}$ = 1.5152 |
| 1.2a | | R | |

TABLE 1-continued

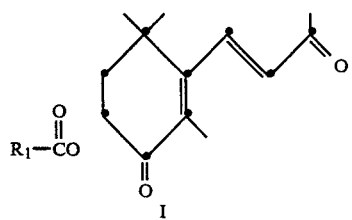

I
racemic mixture

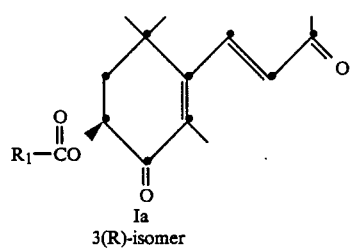

Ia
3(R)-isomer

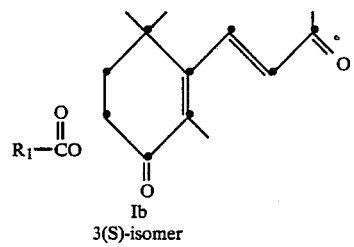

Ib
3(S)-isomer

TABLE 1-continued

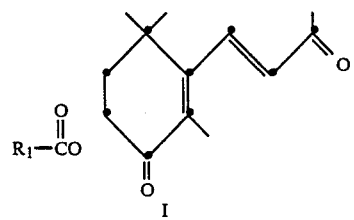

I
racemic mixture

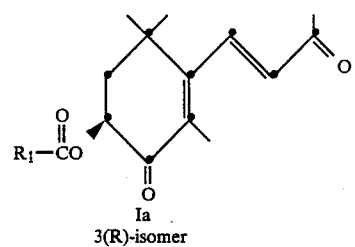

Ia
3(R)-isomer

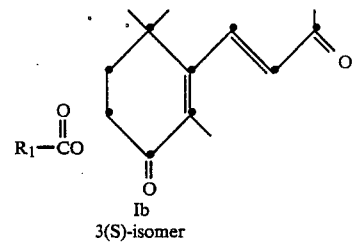

Ib
3(S)-isomer

| No. | $R_1$ | Configuration at C-3 | physical data |
|---|---|---|---|
| 1.2b | | S | |
| 1.3 | i-$C_3H_7$— | racemic mixture | $n_D^{20}$ = 1.5118 |
| 1.3a | | R | |
| 1.3b | | S | |
| 1.4 | n-$C_4H_9$— | racemic mixture | bp 150/4 mbar |
| 1.4a | | R | |
| 1.4b | | S | |
| 1.5 | sec-Butyl | racemic mixture | $n_D^{20}$ = 1.5110 |
| 1.5a | | R | |
| 1.5b | | S | |
| 1.6 | i-Butyl | racemic mixture | $n_D^{20}$ = 1.5078 |
| 1.6a | | R | |
| 1.6b | | S | |
| 1.7 | t-Butyl | racemic mixture | $n_D^{20}$ = 1.5070 |
| 1.7a | | R | |
| 1.7b | | S | |
| 1.8 | Et $OCH_2$— | racemic mixture | mp. 59–60° C. |
| 1.8a | | R | |
| 1.8b | | S | |
| 1.9 | n-Hexyl- | racemic mixture | bp. 150°/4 mbar |
| 1.9a | | R | |
| 1.9b | | S | |
| 1.10 | sec-Hexyl- | racemic mixture | |
| 1.10a | | R | |
| 1.10b | | S | |
| 1.11 | neopentyl- | racemic mixture | |
| 1.11a | | R | |
| 1.11b | | S | |
| 1.12 | $CH_3OCH_2$— | racemic mixture | mp. 87–89° C. |
| 1.12a | | R | |
| 1.12b | | S | |
| 1.13 | $CH_3OCH_2CH_2$— | racemic mixture | |
| 1.13a | | R | |
| 1.13b | | S | |
| 1.14 | $CH_3$— | racemic mixture | mp. 65–66° C. |
| 1.14a | | R | |
| 1.14b | | S | |

| No. | $R_1$ | Configuration at C-3 | physical data |
|---|---|---|---|
| 1.15 | ◁ (cyclopropyl) | racemic mixture | |
| 1.15a | | R | |
| 1.15b | | S | |
| 1.16 | $H_3C$ $CH_3$ / Cl Cl (2,2-dichloro-3,3-dimethylcyclopropyl) | racemic mixture | |
| 1.16a | | R | |
| 1.16b | | S | |
| 1.17 | $C_2H_5OCH_2$— | racemic mixture | |
| 1.17a | | | |
| 1.17b | | | |
| 1.18 | n-pentyl | racemic mixture | |

Preparation of the compound

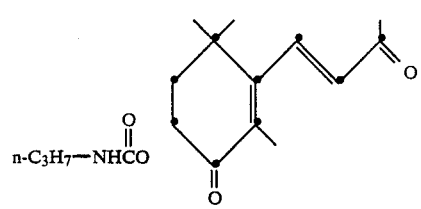

racemic 3-[n-(-propyl-carbamoyloxy)]-4-keto-β-ionon (Compound No. 2.1 of Table 2)

A stirred solution of 0.85 g rac. 3-hydroxy-4-keto-β-ionone in 5 ml abs. toluene is treated with a catalytic amount of 1,4-diazabicyclo-[2.2.2]octane, followed by 0.36 ml of n-propyl-isocyanate. Stirring is continued overnight. After evaporation of the solvent, the residue is purified by column-chromatography (silicagel; hexane/ethyl acetate 1:1) affording the title compound with a mp. of 94°-96°. The compounds listed in the following table 2 can be prepared according to the method described above.

TABLE 2

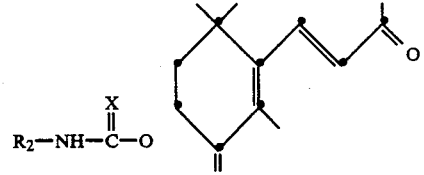

I
racemic mixture

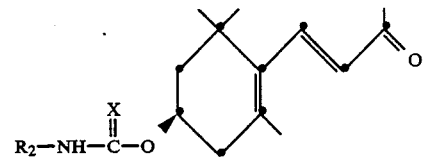

Ia
3(R)-isomer

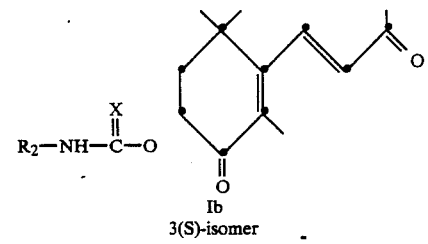

Ib
3(S)-isomer

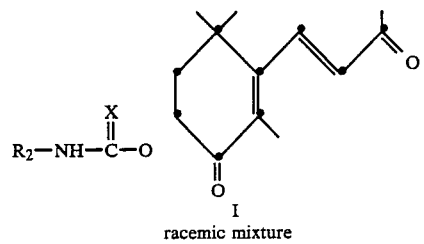

I
racemic mixture

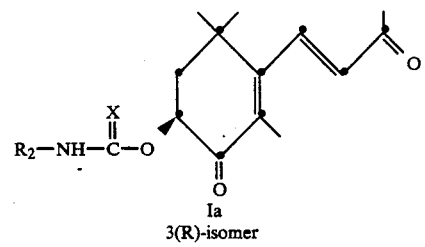

Ia
3(R)-isomer

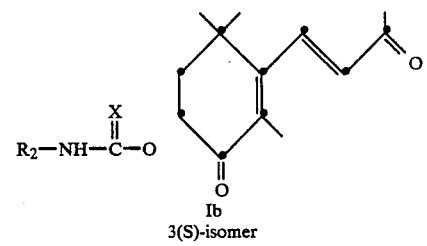

Ib
3(S)-isomer

| No. | X | R$_2$ | Configuration at C-3 | physical data |
|---|---|---|---|---|
| 2.1 | O | n-C$_3$H$_7$— | racemic | m.p. 94–96° C. |
| 2.1a | | | R- | |
| 2.1b | | | S- | |
| 2.2 | O | ethyl | racemic | |
| 2.2a | | | R | |
| 2.2b | | | S | |
| 2.3 | O | i-propyl | racemic | |
| 2.3a | | | R | |
| 2.3b | | | S | |
| 2.4 | O | n-butyl | racemic | |
| 2.4a | | | R | |
| 2.4b | | | S | |
| 2.5 | O | sec-butyl | racemic | |
| 2.5a | | | R | |
| 2.5b | | | S | |
| 2.6 | O | i-butyl | racemic | |
| 2.6a | | | R | |
| 2.6b | | | S | |
| 2.7 | O | t-butyl | racemic | |
| 2.7a | | | R | |
| 2.7b | | | S | |
| 2.8 | O | n-hexyl | racemic | |
| 2.8a | | | R | |
| 2.8b | | | S | |
| 2.9 | O | neopentyl | racemic | |
| 2.9a | | | R | |
| 2.9b | | | S | |
| 2.10 | O | methyl | racemic | |
| 2.10a | | | R | |
| 2.10b | | | S | |
| 2.11 | O | cyclopropyl | racemic | |
| 2.11a | | | R | |
| 2.11b | | | S | |
| 2.12 | S | methyl | racemic | |
| 2.12a | | | R | |
| 2.12b | | | S | |
| 2.13 | S | ethyl | racemic | |
| 2.13a | | | R | |
| 2.13b | | | S | |
| 2.14 | S | n-propyl | racemic | |
| 2.14a | | | R | |
| 2.14b | | | S | |
| 2.15 | S | n-butyl | racemic | |
| 2.15a | | | R | |
| 2.15b | | | S | |
| 2.16 | S | n-hexyl | racemic | |
| 2.16a | | | R | |
| 2.16b | | | S | |
| 2.17 | S | sec-butyl | racemic | |
| 2.17a | | | R | |
| 2.17b | | | S | |
| 2.18 | S | i-butyl | racemic | |
| 2.18a | | | R | |
| 2.18b | | | S | |
| 2.19 | S | neopentyl | racemic | |
| 2.19a | | | R | |
| 2.19b | | | S | |
| 2.20 | S | cyclopropyl | racemic | |
| 2.20a | | | R | |
| 2.20b | | | S | |

2. Formulation Examples

Formulation Examples for liquid active ingredients of the formula I (throughout, percentages are by weight)

| 2.1. Emulsifiable concentrates | (a) | (b) | (c) |
|---|---|---|---|
| a compound of Tables 1 or 2 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2.2. Solutions | (a) | (b) | (c) | (d) |
|---|---|---|---|---|
| a compound of Tables 1 or 2 | 80% | 10% | 5% | 95% |
| ethylene glycol monomethyl ether | 20% | — | — | — |
| polyethylene glycol 400 (mol wt) | — | 70% | — | — |
| N-methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of microdrops.

| 2.3. Granulates | (a) | (b) |
|---|---|---|
| a compound of Tables 1 or 2 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| a compound of Tables 1 or 2 | 2% | 5% |
| highly dispersed silicic acid | 1% | 5% |
| talcum | 97% | — |
| kaolin | — | 90% |

Ready-for-use dusts are obtained by intimately mixing the carriers with the active ingredients.

| 2.5. Wettable powders | (a) | (b) | (c) |
|---|---|---|---|
| a compound of Tables 1 or 2 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentrations.

| 2.6. Emulsifiable concentrate | |
|---|---|
| a compound of Tables 1 or 2 | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| a compound of Tables 1 or 2 | 5% | 8% |
| talcum | 95% | — |
| kaolin | — | 92% |

Ready-for-use dusts are obtained by mixing the active ingredient with the carriers, and grinding the mixture in a suitable mill.

| 2.8. Extruder granulate | |
|---|---|
| a compound of Tables 1 or 2 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Tables 1 or 2 | 3% |
| polyethylene glycol 200 (mol wt) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| a compound of Tables 1 or 2 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

3.1. Inhibition of Sporangial Germination

The substances ($10^2$–$10^{-10}$ ppm) were added to 1% water agar and poured into petri dishes. After cooling, the media were inoculated with 100 μl of a suspension of sporangia (10⁶ s/ml) and incubated at 18° C. during 16 hours. The germinated sporangia were counted under the microscope.

3.1.1. Inhibition of Blue Mold on Excised Leaves of Tobacco

Leaves from plants (2-leaf stage) were excised from 14 Kentucky tobacco plants. The petioles of the leaves were placed into 15 ml of a solution of 1% ethanol in water or 15 ml of a solution of 3-n-butyroyloxy-β-ionone (or another derivative) in 1% ethanol for 1 hour under cool white fluorescent light (ca. 100 μE/sec/cm²) in a growth chamber at 20° C. Each leaf was then inoculated with 6 ca. 5-μl drops of a sporangial suspension of *Peronospora tabacina* isolate Ky 14 (10⁴ sporangia/ml). The inoculated leaves were kept in darkness at 100% relative humidity for 24 hours, removed from the solutions, placed on moist filter paper in glass petri dishes for 6–7 days (14 hours light, 100 μE/sec./cm², and 10 hour dark in a growth chamber at 20° C. Leaves were then rated for lesion development on a scale of 0–4. After rating, leaves were turned over to their adaxial surface and placed in the dark for 18 hr to permit sporulation.

RESULTS

Inhibition of Sporangial Germination

Activity of 4-keto-β-ionone derivatives as inhibitors of sporangial germination in *Peronospora tabacina*.

3.1.2. Inhibition of Blue Mold on Tobacco plants 8-week old Kentucky 14 tobacco plants were sprayed with a wettable powder formulation of the test compounds. 2 days later, the plants were inoculated with a sporangia suspension of *Peronospora tabacina* (10 sporangia/ml). The plants were kept for 20 hours in the dark at 25° C. and 100% humidity and then further incubated at 25° C. The symptoms were recorded 11 to 13 days later.

Compounds of Table 3 exhibited a good protection, e.g. less than 10% of the attack on control plants with compounds No. 1.2, 1.17 and 2.1.

Results of test 3.1.3.

TABLE 3

| Compound No. | ED₅₀(ppm) |
|---|---|
| 1.2 | 2 · 10⁻⁶ |
| 1.3 | 7 · 10⁻³ |
| 1.4 | 3 · 10⁻³ |
| 1.5 | 1.6 · 10⁻⁷ |
| 1.6 | 2.3 · 10⁻⁸ |
| 1.7 | 1.3 · 10⁻⁶ |
| 1.9 | 4 · 10⁻⁵ |
| 1.17 | 3.4 · 10⁻¹⁰ |
| 2.1 | 4.8 · 10⁻⁶ |

3.2. Action against *Plasmopara viticola* on vines

Residual protective action

Vine seedlings in the 4–5 leaf stage were sprayed with a spray mixture (1000 ppm a.i.) prepared from a wettable powder formulation of the test compound. After 24 hours the treated plants were infected with a sporangia suspension of the fungus. Fungus attack was evaluated after incubation for 6 days at 95–100% relative humidity and 20° C.

Fungus attack on plants treated with compounds No. 1.2, 1.3, 1.4, 1.9, 1.12 and 1.14 (table 1) was less than 10% of the attack on untreated plants.

3.3. Action against *Erysiohe graminis* on wheat

Residual protective action

Ten seeds of Coker 68-15 were planted into each pot (45 ml) filled with TKS-1 soil containing 5% of sand. There were three pots per treatment. Seeds were sown in the centre of each pot and were covered with a clear plastic cylinder (7.6 cm diameter, 22.5 cm tall). The cylinders were topped with filter paper secured with rubber bands to prevent accidental infection with *Erysiphe graminis*. Greenhouse temperature was maintained at 18° to 24° C. The treatments were applied when the plants had three leaves using a SPRA-TOOL aerosol. Products were first dispersed in water and the suspension (250 g/ha) was then applied until a uniform coverage of the foliage was achieved. In preliminary experiments, suspension concentrations were defined so that the amounts of product applied were equivalent to those applied in the field. Nine days after application, test plants were inoculated by having plants with sporulating lesions shaken over them. Disease development was then estimated at frequent intervals by assessing the percentage of leaf area covered by lesions.

Compounds of table 1 and 2 exhibited a good protection, e.g. less than 10% disease with compound No. 1.2.

What we claim is:

1. A 3-acyloxy-4-keto-β-ionone derivative of the formula I

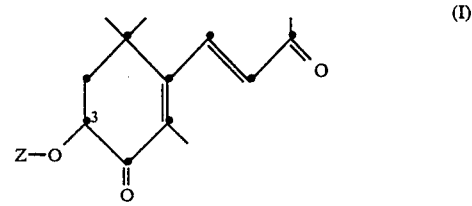

wherein Z is either the radical

in which R₁ represents C₃–C₅-alkyl, C₁–C₅ alkoxy-C₁–C₅ alkyl having a maximum number of 6 carbon atoms, cyclopropyl or cyclopropyl which is substituted by methyl or by halogen or represents the radical

wherein R₂ represents C₁–C₅alkyl, C₁–C₅ alkoxy-C₁–C₅ alkyl having a maximum number of 6 carbon atoms, cyclopropyl or cyclopropyl which is substituted by methyl or by halogen and X represents either oxygen or sulphur.

2. Compounds according to claim 1, wherein Z is the radical

3. Compounds of claim 2 wherein $R_1$ is $C_3$–$C_5$ alkyl.

4. Compounds according to claim 2, wherein $R_1$ represents n-propyl, n-butyl, n-pentyl.

5. Racemic 3(RS)-n-butyroyloxy-4-keto-β-ionone according to claim 4.

6. 3(R)-n-butyroyloxy-4-keto-β-ionone according to claim 4.

7. 3(S)-n-butyroyloxy-4-keto-β-ionone according to claim 4.

8. Racemic 3(RS)-[n-(N-propyl-carbamoyloxy)]-4-keto-β-ionone according to claim 1.

9. Racemic 3(RS)-[ethoxyacetyloxy]-4-keto-β-ionone according to claim 1.

10. Compounds according to claim 1, wherein Z is the radical

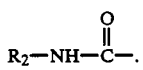

11. A microbicidal composition for controlling phytopathogenic fungi comprising as active ingredient an effective amount of a compound according to claim 1, together with a suitable carrier.

12. A method of controlling phytopathogenic fungi which comprises applying a microbicidally effective amount of a 3-acyloxy-4-keto-β-ionone derivative of the formula I, according to claim 1, wherein Z is either the radical

in which $R_1$ represents $C_1$–$C_5$ alkyl, $C_1$–$C_5$ alkoxy-$C_1$–$C_5$ alkyl having a maximum number of 6 carbon atoms, cyclopropyl or cyclopropyl which is substituted by methyl or by halogen or represents the radical

wherein $R_2$ represents $C_1$–$C_5$ alkoxy-$C_1$–$C_5$ alkyl having a maximum number of 6 carbon atoms, cyclopropyl or cyclopropyl which is substituted by methyl or by halogen and X represents either oxygen or sulphur.

13. A method according to claim 12 wherein the microorganisms to be controlled are phytopathogenic fungi, especially Oomycetes.

14. A method according to claim 13 wherein the phytopathogenic fungi to be controlled are *Peronospora tabacina*.

15. A method according to claim 13 wherein the phytopathogenic fungi to be controlled are *Plasmopara viticola*.

16. A method according to claim 13 wherein the phytopathogenic fungi to be controlled are *Erysiphe graminis*.

* * * * *